(12) United States Patent
Martin et al.

(10) Patent No.: US 10,961,235 B2
(45) Date of Patent: Mar. 30, 2021

(54) CRYSTALLINE FORM OF MASITINIB (71) Applicant: Sandoz AG, Basel (CH)

(72) Inventors: Nolwenn Martin, Kundl (AT); Diana Fischer-Daut, Kundl (AT)

(*) Notice: Subject to any disclaimer, the term of this patent is extended or adjusted under 35 U.S.C. 154(b) by 0 days.

(21) Appl. No.: 16/498,483

(22) PCT Filed: Mar. 22, 2018

(86) PCT No.: PCT/EP2018/057232
§ 371 (c)(1),
(2) Date: Sep. 27, 2019

(87) PCT Pub. No.: WO2018/177854
PCT Pub. Date: Oct. 4, 2018

(65) Prior Publication Data
US 2020/0102297 A1 Apr. 2, 2020

(30) Foreign Application Priority Data

Mar. 31, 2017 (EP) .................................. 17164287
Aug. 9, 2017 (EP) .................................. 17185532
Oct. 4, 2017 (EP) .................................. 17194734

(51) Int. Cl.
*C07D 417/04* (2006.01)
*A61K 9/20* (2006.01)

(52) U.S. Cl.
CPC .......... *C07D 417/04* (2013.01); *A61K 9/2018* (2013.01); *A61K 9/2054* (2013.01); *C07B 2200/13* (2013.01)

(58) Field of Classification Search
CPC .................. C07D 417/04; C07D 2200/13
See application file for complete search history.

(56) References Cited

FOREIGN PATENT DOCUMENTS

| EP | 2886543 A1 | 6/2015 |
| WO | 2004014903 A1 | 2/2004 |
| WO | 2008098949 A2 | 8/2008 |
| WO | 2017016512 A1 | 2/2017 |

OTHER PUBLICATIONS

Machine translation of WO 2017016512, published Feb. 2, 2017. (Year: 2017).*
International Search Report and Written Opinion for PCT/EP2018/057232, dated Apr. 20, 2018, 16 pages.
Pecharsky and Zavalij, Fundamentals of Powder Diffraction and Structural Characterization of Minerals, Kluwer Academic Publishers, 2003, p. 3.
Teng, Yue, et al., Systematical approach of formulation and process development using roller compaction, European Journal of Pharmaceutics and Biopharmaceutics, 2009, vol. 73, pp. 219-229.

* cited by examiner

*Primary Examiner* — Noble E Jarrell
(74) *Attorney, Agent, or Firm* — Luedeka Neely Group, P.C.

(57) ABSTRACT

The present invention relates to a polymorphic form of masitinib mesylate, processes for its preparation, pharmaceutical compositions comprising it and their medical use.

14 Claims, 5 Drawing Sheets

CRYSTALLINE FORM OF MASITINIB

This application is a Section 371 national phase entry of PCT application PCT/EP2018/057232, filed Mar. 22, 2018. This application also claims the benefit of the earlier filing dates of European patent application 17164287.9, filed Mar. 31, 2017, European patent application 17185532.3, filed Aug. 9, 2017, and European patent application 17194734.4, filed Oct. 4, 2017.

FIELD OF INDUSTRIAL APPLICABILITY

The present invention relates to a polymorphic form of masitinib mesylate, processes for its preparation, compositions comprising it and their medical use.

BACKGROUND OF THE DISCLOSURE

Masitinib is a tyrosine kinase inhibitor with specificity for c-kit, but it also targets the non-receptor tyrosine kinases Lyn and FGFR3 to a lower extent (Dubreuil et al. 2009). It has been suggested for the treatment of cancer (gastrointestinal stromal tumor (GIST), pancreatic cancer, multiple myeloma (MM), metastatic melanoma), inflammatory diseases (mastocytosis, rheumatoid arthritis (RA) and asthma), and CNS disorders (Alzheimer's disease (AD), multiple sclerosis (MS)) in human subjects. It is already approved as a veterinary medicine for the treatment of mast cell tumors and is in discussion for approval for the treatment of severe systemic mastocytosis. Masitinib is disclosed in WO 2004/014903 A2.

WO 2008/098949 A2 discloses a crystalline form of masitinib mesylate, hereinafter called crystal form I, characterized by an X-ray powder diffraction pattern (XRPD). The positions of the XPRD peaks are disclosed on page 23 and include peaks at 2-Theta positions of 7.269, 9.120, 11.038, 13.704, 14.481 and 18.224°, among others. It is also disclosed that the form remains dry at 80% relative humidity (RH) and thermodynamically stable at temperatures below 200° C.

In the file history of European patent application 11170200.7, applicant's response to the eESR dated Mar. 20, 2012, (hereinunder called "response to the eESR"), two more polymorphic forms of masitinib mesylate are mentioned and named DRX2 and DRX3. DRX2 and DRX3 are described as having physicochemical properties that render them less suitable for pharmaceutical dosage forms than DRX1. In the response to the eESR it is concluded that DRX1 should be the "ideal" candidate for developing a pharmaceutical dosage form, even though it is described that DRX1 is mildly hygroscopic with a 4.3 weight-% increase observed between 0% RH and 80% RH. The response to the eESR does not describe how DRX2 and DRX3 could be obtained.

EP2886543 A1 discloses a crystalline form of a salt of masitinib with methane sulfonic acid characterized by a XRPD pattern comprising peaks at 2-Theta values of 7.8, 8.3, 10.9, 11.3, 24.0, and 33.2, called "form H". Form H is described to be a hydrated form with low hygroscopicity. In a comparative example the preparation of DRX2 from methanol is describes, as well as the transition of DRX2 to DRX1 upon heating, confirming the finding of the response to the eESR that DRX2 shows problems with polymorphic conversion at temperatures above 25° C.

WO2017/016512A1 discloses another crystalline form of masitinib mesylate, called "form A", characterized by a XRPD pattern comprising characteristic peaks at 2-Theta values of 18.2°, 20.7° and 21.1°, but no characteristic peaks below a 2-Theta value of 10.0°. It is also stated that the hygroscopicity of crystal form A was remarkably reduced compared to DRX1 and that this form was therefore convenient for medicaments preparation and long-term storage. The TGA thermogram of crystal form A represented in FIG. 3 shows a loss of about 6.4 weight-% upon heating the sample between 33° C. and 100° C., corresponding to a loss of about 2 mol water. Additionally, a reversible loss of about 5 weight-% water below 10% RH is represented in the gravimetric moisture sorption/desorption curves in FIG. 6, indicating that crystal form A is a hydrated form. In the gravimetric moisture sorption (GMS) curve provided in FIG. 6 a water uptake of from 4 weight-% to 6 weight-% in the range of from 15% RH to 80% RH is observed.

There remains thus a need for a further polymorph of masitinib mesylate suitable for the development of pharmaceutical dosage forms, preferably one with improved properties. Moreover, as hygroscopic solid forms pose a limitation to the types of pharmaceutical dosage forms which can be prepared from them, for the types of excipients which can be used in combination with them and for the conditions and processes, which can be employed during the preparation of a pharmaceutical dosage form comprising a hygroscopic solid form of masitinib mesylate, there is thus a need for a solid form of masitinib mesylate, which is non-hygroscopic at a range of relative humidity which is typical of the regular working conditions encountered during finished dosage form preparation.

SUMMARY OF THE DISCLOSURE

The present disclosure provides a new crystalline form of masitinib mesylate, which is herein called form M, and a process for its preparation. Form M can be obtained in high polymorphic purity and it can be used in the manufacture of pharmaceutical dosage forms comprising masitinib mesylate.

ABBREVIATIONS

XRPD X-ray powder diffractogram

GMS gravimetric moisture sorption

RH relative humidity w-% weight percent

DETAILED DESCRIPTION OF THE DISCLOSURE

The disclosure relates to a crystalline form of masitinib mesylate, which is described and characterized herein in more detail.

Definitions

As used herein "polymorph" refers to crystalline forms having the same chemical composition but different spatial arrangements of the molecules, atoms, and/or ions forming the crystal.

As used herein "hydrate" refers to a crystalline form of a molecule that further comprises molecules of water incorporated into the crystalline lattice structure. The water molecules in the hydrate may be present in a regular arrangement and/or a non-ordered arrangement. The hydrate may comprise either a stoichiometric or a nonstoichiometric amount of the water molecules. For example, a hydrate with a nonstoichiometric amount of water molecules may result from partial loss of water from the stoichiometric hydrate. Hydrates may occur as dimers or oligomers comprising more than one molecule of masitinib within the crystalline lattice structure.

As used herein "amorphous" refers to a solid form of a molecule that is not crystalline. An amorphous solid does not display a definite X-ray diffraction pattern.

As used herein, the term "substantially pure" with reference to a particular polymorphic form means that the polymorphic form includes less than 10%, preferably less than 5%, more preferably less than 3%, most preferably less than 1% by weight of any other physical forms of the compound.

As used herein the term "masitinib mesylate" refers to the monomesylate salt of masitinib, wherein about one mole of masitinib in its protonated form is associated with one mole of mesylate anions via ionic interaction. This term includes hydrated and anhydrated forms of the salt masitinib mesylate, unless specified further.

As used herein, the term "room temperature" refers to a temperature in the range of from 20 to 30° C., in particular 22° C. to 26° C. As used herein, standard conditions mean room temperature and 20-70% relative humidity, more preferably 30-60% relative humidity and most preferably about 40% relative humidity.

The term "reflection" with regards to powder X-ray diffraction as used herein, means peaks in an X-ray powder diffractogram, which are caused at certain diffraction angles (Bragg angles) by constructive interference from X-rays scattered by parallel planes of atoms in solid material, which are distributed in an ordered and repetitive pattern in a long-range positional order. Such a solid material is classified as crystalline material, whereas amorphous material is defined as solid material, which lacks long-range order and only displays short-range order, thus resulting in broad scattering. According to literature, long-range order e.g. extends over approximately 100 to 1000 atoms, whereas short-range order is over a few atoms only (see "*Fundamentals of Powder Diffraction and Structural Characterization of Materials*" by Vitalij K. Pecharsky and Peter Y. Zavalij, Kluwer Academic Publishers, 2003, page 3).

Crystalline forms of masitinib mesylate may be referred to herein as being characterized by an X-ray powder diffractogram "as shown in" a figure. The person skilled in the art understands that factors such as variations in instrument type, response and variations in sample directionality, sample concentration, sample purity, sample history and sample preparation may lead to variations, for example relating to the exact reflection positions and intensities. However, a comparison of the graphical data in the figures herein with the graphical data generated for an unknown physical form and the confirmation that two sets of graphical data relate to the same crystal form is well within the knowledge of a person skilled in the art.

As used herein, the term "about" means within a statistically meaningful range of a value. Such a range can be within an order of magnitude, typically within 10%, more typically within 5%, even more typically within 1% and most typically within 0.1% of the indicated value or range. Sometimes, such a range can lie within the experimental error, typical of standard methods used for the measurement and/or determination of a given value or range.

As used herein, the term "wet granulation" refers to the general process of using a granulation liquid in a granulation process to subsequently form granules comprising the active pharmaceutical ingredient, as discussed in "Die Tablette" $2^{nd}$ edition, Chapter 4.4, which is herein incorporated by reference.

As used herein, the term "dry granulation" refers to the general process of using a dry mixing process of the active pharmaceutical with at least one excipient and a subsequent compression or compaction step to form granules comprising the active pharmaceutical ingredient, as discussed in "Die Tablette" $2^{nd}$ edition, Chapter 4.2, which is herein incorporated by reference. A preferred dry granulation process is roller compaction.

The term "direct compression" used herein means blending of active pharmaceutical ingredient (i.e. masitinib form M as API), with other ingredients (pharmaceutically acceptable excipients) and direct compaction of the resultant mixture as discussed in "Die Tablette" $2^{nd}$ edition, Chapter 4.1, which is herein incorporated by reference. In direct compression, a dry formulation containing the API masitinib form M and further ingredients are typically processed by applying a sufficient force by the punches of a tablet press on a powder to compact it into a tablet, notably a tablet core.

Crystal Form M

Figure 1:
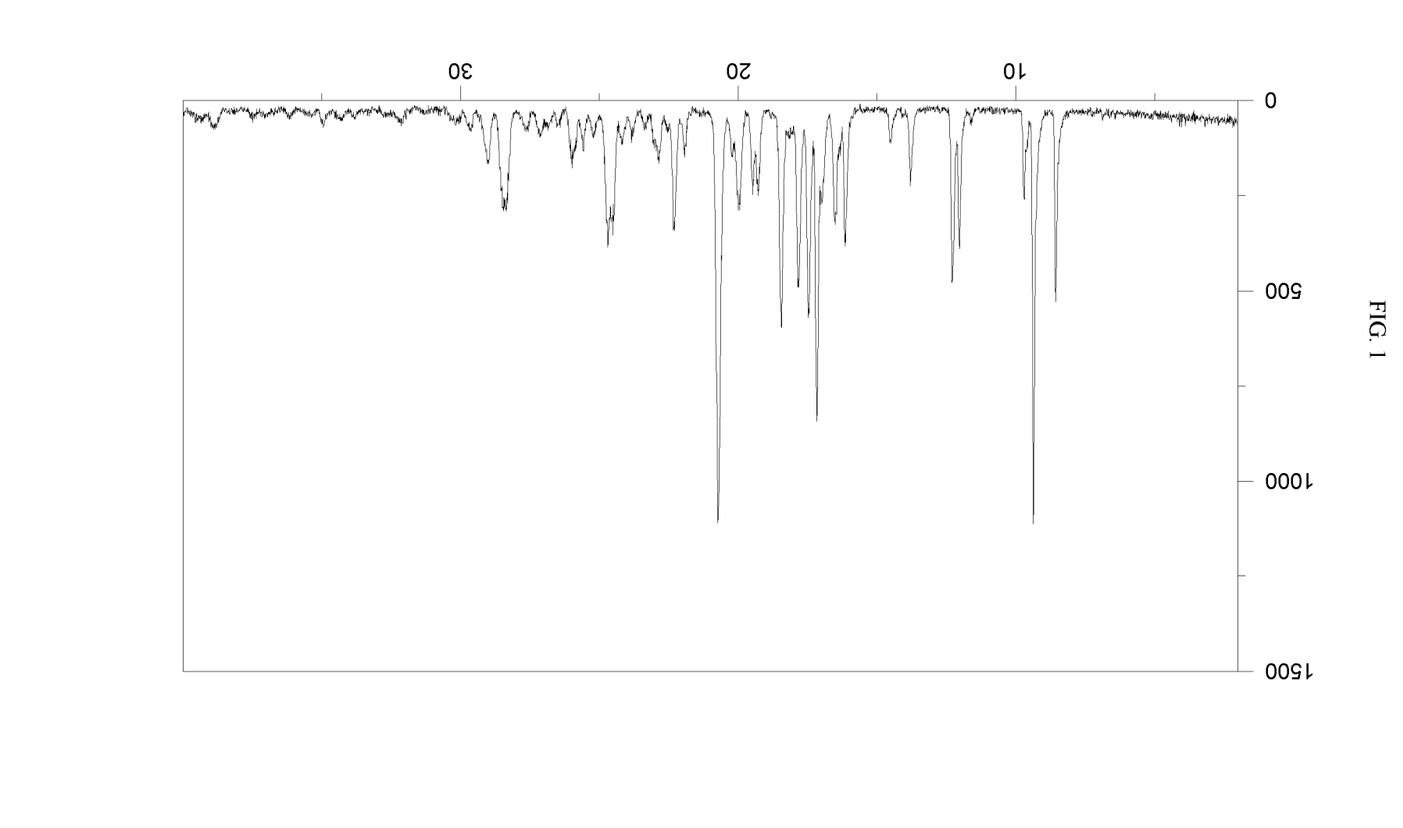
FIG. 1 illustrates the x-ray powder diffraction pattern of crystalline form M of masitinib mesylate.
Figure 2:
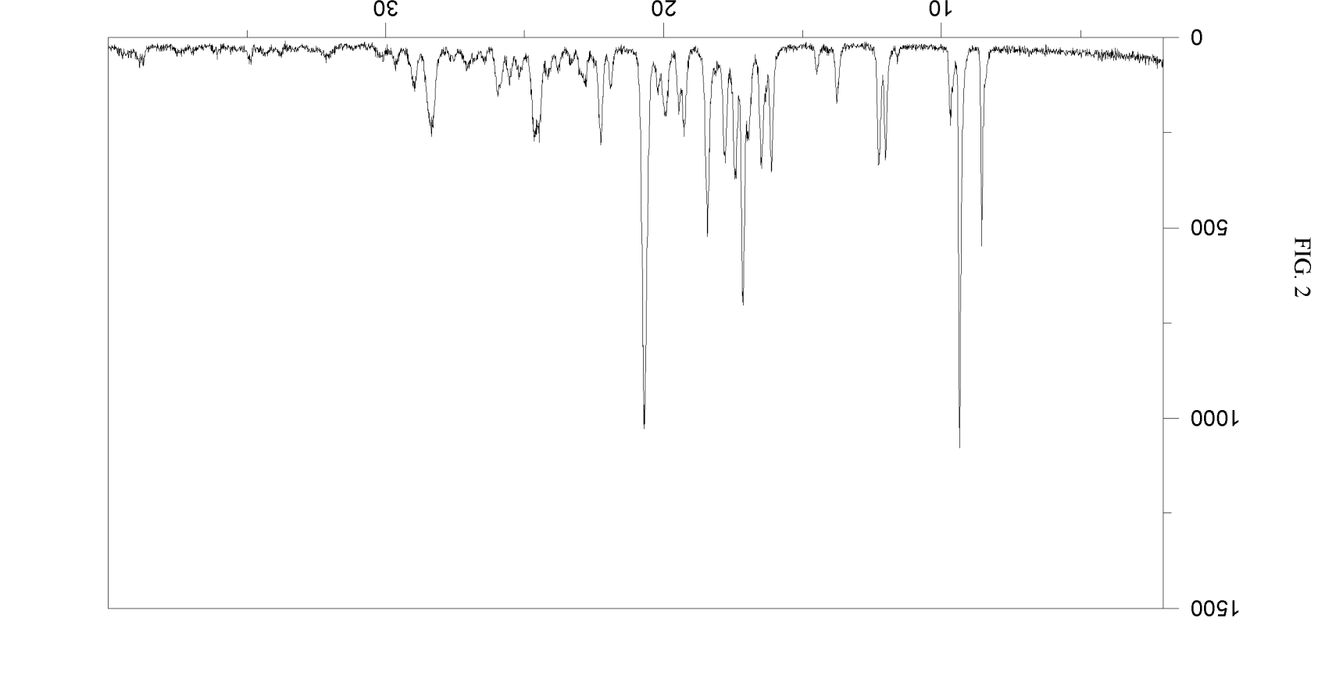
FIG. 2 illustrates the x-ray powder diffraction pattern of crystalline form M of masitinib mesylate after storage for 8 weeks at 40° C.

The present invention provides a crystalline form of masitinib mesylate having an X-ray powder diffraction pattern (XRPD) comprising the peaks as mentioned in claim 1, for example a crystalline form of masitinib mesylate having a XRPD pattern substantially the same as the XRPD pattern shown in FIG. 1.

The term "essentially the same" with reference to X-ray powder diffraction peak positions means that typical peak position and intensity variability are taken into account. For example, a typical precision of the 2-Theta values is in the range of ±0.2° 2-Theta, such as in the range of ±0.1° 2-Theta. Thus, a diffraction peak that usually appears at 8.6° 2-Theta for example can appear between 8.4° and 8.8° 2-Theta on most X-ray powder diffractometers, and typically appears between 8.5° and 8.7° 2-Theta under standard conditions, that is when measured at a temperature in the range of from 15 to 25° C. with Cu—Kalpha$_{1,2}$ radiation having a wavelength of 0.15419 nm.

Furthermore, a person skilled in the art will appreciate that relative peak intensities will show inter-apparatus variability as well as variability due to degree of crystallinity, preferred orientation, sample preparation and other factors known to those skilled in the art and should be taken as qualitative measure only. Consequently, it is to be understood that the crystal form of the present invention is not limited to the crystal form that provides X-ray powder diffraction patterns completely identical to the X-ray powder diffraction pattern depicted in the accompanying figure disclosed herein. Any crystal forms that provide X-ray powder diffraction patterns substantially identical to the one disclosed in the accompanying Figure fall within the scope of the present invention. The ability to ascertain substantial identities of X-ray powder diffraction patterns is within the purview of one of ordinary skill in the art.

In one embodiment of the present invention, crystalline form M of masitinib mesylate is provided in substantially pure form.

Crystalline form M of masitinib mesylate is a hydrate, i.e. it may include from 0.1 w-% to 4.0 w-% of water, preferably from 0.1 w-% to 3.0 w-% of water, more preferably from 0.1 w-% to 2.5 w-% of water, in particular at room temperature and at 40% RH. It may also contain solvents other than water, which solvents were used during its preparation, preferably from 0 w-% to 0.5 w-%, such as from 0.001 w-% to 0.3 w-%, preferably from 0.001 w-% to 0.25 w-%, in particular from 0.001 w-% to 0.20 w-%, such as from 0.001 w-% to 0.15 w-%. Water and solvent content can be determined by thermogravimetric analysis and the skilled person will understand to distinguish between the two, if necessary, using additional techniques, such as NMR. A preferred form M of masitinib mesylate includes at most 0.25 w-% methanol as residual solvent, preferably at most 0.20 w-% methanol, and most preferably at most 0.15 w-% methanol.

In one embodiment crystalline form M of masitinib mesylate can be characterized by having a XRPD pattern comprising reflections at 2-Theta angles of 8.6±0.2°, 9.4±0.2°, 9.7±0.2°, 12.3±0.2° and 17.2±0.2°, when measured at room temperature using Cu—Kα$_{1,2}$ radiation having a wavelength of 0.15419 nm. The XRPD pattern of crystalline form M of masitinib mesylate may be further characterized by comprising one or more additional reflections at 2-Theta angles of 12.0±0.2°, 16.1±0.2°, 16.5±0.2°, 17.5±0.2°, 17.8±0.2°, 18.4±0.2° and/or 20.7±0.2°, when measured at room temperature with Cu—Kα$_{1,2}$ radiation having a wavelength of 0.15419 nm, for example when measured at 22° C. and at 25% RH.

Crystalline form M of masitinib mesylate can also be characterized by having a XRPD pattern comprising reflections at 2-Theta angles of 8.6±0.1°, 9.4±0.1°, 9.7±0.1°, 12.3±0.1° and 17.2±0.1°, when measured at room temperature using Cu—Kα$_{1,2}$ radiation having a wavelength of 0.15419 nm. The XRPD pattern of crystalline form M of masitinib mesylate may be further characterized by comprising one or more additional reflection(s) at 2-Theta angles of 12.0±0.1°, 16.1±0.1°, 16.5±0.1°, 17.5±0.1°, 17.8±0.1°, 18.4±0.1° and/or 20.7±0.1°, when measured at room temperature with Cu—Kα$_{1,2}$ radiation having a wavelength of 0.15419 nm, for example when measured at 22° C. and at 25% RH.

Crystalline form M of masitinib mesylate can also be characterized by having a XRPD pattern comprising five or more reflections, such as 6 reflections, 7 reflections, 8 reflections or 10 reflections, at 2-Theta angles selected from 8.6±0.2°, 9.4±0.2°, 9.7±0.2°, 12.0±0.2°, 12.3±0.2°, 16.1±0.2°, 16.5±0.2°, 17.2±0.2°, 17.5±0.2°, 17.8±0.2°, 18.4±0.2° and 20.7±0.2°, when measured at room temperature with Cu—Kα$_{1,2}$ radiation having a wavelength of 0.15419 nm. Crystalline form M of masitinib mesylate can also be characterized by having a XRPD pattern comprising five or more reflections such as 6 reflections, 7 reflections, 8 reflections or 10 reflections, at 2-Theta angles selected from 8.6±0.1°, 9.4±0.1°, 9.7±0.1°, 12.0±0.1°, 12.3±0.1°, 16.1±0.1°, 16.5±0.1°, 17.2±0.1°, 17.5±0.1°, 17.8±0.1°, 18.4±0.1° and 20.7±0.1°, when measured at room temperature with Cu—Kα$_{1,2}$ radiation having a wavelength of 0.15419 nm.

Alternatively or additionally, crystalline form M of masitinib mesylate can be characterized by having a XRPD pattern essentially the same as displayed in FIG. 1, when measured at room temperature with Cu—Kα$_{1,2}$ radiation having a wavelength of 0.15419 nm.

A listing of peaks with a relative intensity above 5%, their heights and relative intensities are reported Table 1 (relative peak intensities can vary due to e.g. inter-apparatus variability, sample crystallinity, sample preparation, etc.):

TABLE 1

XRPD reflections and corresponding relative intensities of crystalline form M of masitinib mesylate in the range of from 2 to 30° 2-Theta; A typical precision of the 2-Theta values is in the range of ±0.2° 2-Theta, preferably of ±0.1° 2-Theta.

| position/°2-theta | relative intensity/% |
|---|---|
| 8.6 ± 0.2 | 47 |
| 9.4 ± 0.2 | 99 |
| 9.7 ± 0.2 | 22 |
| 12.0 ± 0.2 | 34 |
| 12.3 ± 0.2 | 42 |
| 13.8 ± 0.2 | 17 |
| 14.5 ± 0.2 | 8 |
| 16.1 ± 0.2 | 31 |
| 16.5 ± 0.2 | 26 |
| 17.2 ± 0.2 | 75 |
| 17.5 ± 0.2 | 50 |
| 17.8 ± 0.2 | 42 |
| 18.4 ± 0.2 | 52 |
| 19.3 ± 0.2 | 20 |
| 19.5 ± 0.2 | 20 |
| 20.0 ± 0.2 | 23 |
| 20.2 ± 0.2 | 11 |
| 20.7 ± 0.2 | 100 |
| 21.9 ± 0.2 | 10 |
| 22.3 ± 0.2 | 28 |
| 22.9 ± 0.2 | 12 |
| 23.8 ± 0.2 | 6 |
| 24.2 ± 0.2 | 8 |
| 24.7 ± 0.2 | 31 |
| 25.2 ± 0.2 | 6 |
| 25.6 ± 0.2 | 9 |
| 26.0 ± 0.2 | 12 |
| 27.1 ± 0.2 | 6 |
| 27.6 ± 0.2 | 5 |
| 28.4 ± 0.2 | 25 |
| 29.0 ± 0.2 | 14 |
| 29.7 ± 0.2 | 5 |

Crystalline form M of masitinib mesylate can also be characterized by having a XRPD pattern comprising reflections at 2-Theta angles of 8.6±0.2°, 9.4±0.2°, 9.7±0.2°, 12.3±0.2° and 17.2±0.2°, when measured at room temperature using Cu—Kα$_{1,2}$ radiation having a wavelength of 0.15419 nm, and further comprising three reflections at 2-Theta angles selected from the positions in the above table which are not in bold. Crystalline form M of masitinib mesylate can also be characterized by having a XRPD pattern comprising reflections at 2-Theta angles of 8.6±0.1°, 9.4±0.1°, 9.7±0.1°, 12.3±0.1° and 17.2±0.1°, when measured at room temperature using Cu-Kα$_{1,2}$ radiation having a wavelength of 0.15419 nm, and further comprising three reflections at 2-Theta angles ±0.1° selected from the positions in the above table which are not in bold.

Moreover, the representative gravimetric moisture sorption (GMS) curve of crystalline form M of masitinib mesylate in the range of from 15 to 80% RH and measured at 25±0.1° C. shows a water content of from 0.1 to 2.5 w-%. According to the GMS measurements crystalline form M of masitinib mesylate is a hydrate of masitinib mesylate. Thus, alternatively or additionally, crystalline form M of masitinib mesylate can be characterized by comprising from 0.1 to 2.5 w-% water in the range of from 15 to 80% relative humidity and at 25±0.1° C. Crystalline form M can also be characterized by having a water uptake from 0.1 to 2.0 w-%, preferably from 0.3 to 1.5 w-%, even more preferably from 0.5 to 1.3 w-% in the range of from 15 to 80% relative humidity and 25±0.1° C.

As can be seen from Table 2 below the weight gain between 15 and 80% RH is only from 0.3 to 1.5 w-%, preferably from 0.5 to 1.3 w-%, for crystalline form M of masitinib mesylate, whereas crystalline form A of masitinib mesylate takes up from 4.0 to 6.0 w-% water in the same range.

TABLE 2

Observations for crystalline form A and crystalline form M of masitinib mesylate during GMS experiments

|  | Crystalline form A | Crystalline form M |
|---|---|---|
| Mass change in the range of from 15-80% RH | 4.0-6.0 w-% | 0.5-1.3 w-% |

In a preferred embodiment, crystal form M is in substantially pure form. Preferably, Form M includes less than 5 w-%, more preferably less than 3 w-%, even more preferably less than 2 w-%, most preferably less than 1 w-% of crystal form I.

Crystalline form I corresponds to form DRX1 as mentioned above and is characterized by a XRPD pattern comprising peaks at 2-Theta angles of 11.04, 14.48, 16.72, 18.22 and 19.25°, when measured at room temperature with Cu—K$\alpha_{1,2}$ radiation having a wavelength of 0.15419 nm. Thus, pure crystalline form M of the present invention may preferably be characterized by an x-ray powder diffraction pattern comprising no significant peak at a 2-Theta angle of 11.04°, when measured at room temperature with Cu—K$\alpha_{1,2}$ radiation having a wavelength of 0.15419 nm. A significant peak is defined as a peak with an average relative intensity of at least 3% of the most intense peak of an XRPD, (results from 10 independent measurements are averaged).

When crystalline form M of the present invention was stored for 8 weeks at 30° C./60% relative humidity, it did not convert to or show detectable traces of crystal form I by XRPD. Thus, the present invention also relates to crystalline form M, wherein after storage for 8 weeks at 30° C./60% relative humidity the x-ray powder diffraction pattern comprises no significant peak at a 2-Theta angle of 11.04°+/−0.03°, when measured at room temperature with Cu—K$\alpha_{1,2}$ radiation having a wavelength of 0.15419 nm.

When crystalline form M of the present invention was stored for 8 weeks at 40° C./75% relative humidity, it did not convert to or show detectable traces of crystal form I by XRPD. Thus, the present invention also relates to crystalline form M, wherein after storage for 8 weeks at 40° C./75% relative humidity the x-ray powder diffraction pattern comprises no significant peak at a 2-Theta angle of 11.04°+/−0.03°, when measured at room temperature with Cu—K$\alpha_{1,2}$ radiation having a wavelength of 0.15419 nm.

In a further preferred embodiment, crystal form M includes less than 5 w-%, more preferably less than 3 w-%, even more preferably less than 2 w-%, most preferably less than 1% by weight of crystal form A.

Crystalline form A is characterized by a XRPD pattern comprising peaks at 2-Theta angles of 20.7±0.2, 18.2±0.2 and 21.1±0.2°, when measured at room temperature with Cu—K$\alpha_{1,2}$ radiation having a wavelength of 0.15419 nm. Thus, pure crystalline form M of the present invention may preferably be characterized by an x-ray powder diffraction pattern comprising no significant peak at a 2-Theta angle of 21.1±0.2°, when measured at room temperature with Cu—K$\alpha_{1,2}$ radiation having a wavelength of 0.15419 nm. A significant peak is defined as a peak with an average relative intensity of at least 3% of the most intense peak of an XRPD, (results from 10 independent measurements are averaged).

The invention also relates to a composition comprising, and in particular consisting of, masitinib mesylate crystalline form M.

Preparation Process

The present invention relates to a process for the preparation of the crystalline form of masitinib mesylate of the invention comprising the steps of
i) providing masitinib free base
ii) (a) dissolving or suspending the material provided in (i) in methanol comprising water and (b) adding methane sulfonic acid,
iii) optionally seeding the mixture with the crystalline form of masitinib mesylate and
iv) subjecting the mixture provided in (iii) to crystallization conditions leading to the formation of the crystalline form of masitinib mesylate
v) isolating the crystalline form of masitinib mesylate,
vi) drying the crystalline form of masitinib mesylate, and
vii) optionally equilibrating the crystalline form of masitinib mesylate with an atmosphere having a relative humidity of from 15% to 80% at a temperature of from 0° C. to 25° C.

The present invention relates also to an alternative process for the preparation of the crystalline form of masitinib mesylate of the invention comprising the steps of
i') providing amorphous masitinib mesylate
ii') dissolving or suspending the material provided in (i') in methanol comprising water
iii') optionally seeding the mixture with the crystalline form of masitinib mesylate and
iv') subjecting the mixture provided in (iii') to crystallization conditions leading to the formation of the crystalline form of masitinib mesylate
v') isolating the crystalline form of masitinib mesylate,
vi') drying the crystalline form of masitinib mesylate, and
vii') optionally equilibrating the crystalline form of masitinib mesylate with an atmosphere having a relative humidity of from 15% to 80% at a temperature of from 0° C. to 25° C.

In step (ii) and (ii') non-anhydrous methanol is added at a temperature in the range of from 10 to 40° C., more preferably in the range of from 20 to 30° C., preferably at ambient pressure. In step (iib) the mole ratio of masitinib and methane sulfonic acid is preferably in the range of from 1.0:1.0 to 1.0:1.3, more preferably in the range of from 1.0:1.0 to 1.0:1.1. Non-anhydrous methanol is methanol comprising water in an amount sufficient to allow masitinib mesylate crystal form M of the present invention to form. The amount of water necessary for the formation of masitinib mesylate crystal form M, which is a hydrate, is low, and usually a bottle of laboratory methanol which has been open for some time will contain sufficient amounts. However, if anhydrous methanol is used for the process, for example for the production of masitinib mesylate crystal form M at a larger scale, such as the production of kg quantities, a low amount of water, such as 0.1 w-%, can be added in order to facilitate formation of masitinib mesylate crystal form M.

Optionally, seed crystals may be added in step (iii) and (iii'). The seed crystals are prepared with the same solvent as the one used in step (iia) or (ii') of the process. In particular, the seed crystals can be prepared according to Example 1-1. The seed crystals are typically added in an amount of 0.1 w-% to 10 w-%, preferably in an amount of 0.5 w-% to 7.0 w-%, most preferably 1.0 w-% 5.0 w-%, on the basis of the total amount of the starting material used in step (i) or (i').

In step (iv) and (iv') the mixture is stirred or allowed to stand at a temperature in the range of from 0 to 30° C., preferably in the range of from 2 to 25° C., typically for a period of time from 5 to 48 hours in order to promote crystallization. It is not critical whether the mixture is stirred or not stirred at this point. After crystallization, the mixture can optionally be cooled to a temperature in the range of from 0 to 20° C., preferably in the range of from 2 to 15° C. to increase the process yield.

Isolation in step (v) and (v') may be performed by using procedures known in the art, such as by filtration, centrifugation, or evaporation of solvent. Moreover, the isolated crystals are dried in step (vi) and (vi'), e.g. under reduced pressure, typically at room temperature. Drying at room temperature is done for at least 6 hours, such as at least 12 hours or at least 24 hours. Reduced pressure is preferably a pressure of below 30 mbar, i.e. conditions that can be achieved by the use of a water-jet vacuum pump. Prolonged drying at a reduced pressure such as 30 mbar can remove traces of methanol remaining from the crystallization step effectively. Analysis by NMR indicated that drying for about 24 hours at a pressure of below 30 mbar removed methanol to a level of below 0.25 w-%. Masitinib mesylate crystal form M wherein residual methanol from the crystallization step has been effectively removed demonstrates improved polymorphic stability upon storage.

Overdrying in step (v) or (v') may result in a partial loss of water from crystal form M. Such a sample can be exposed, for example for a period of more than 60 minutes, such as for more than 6 hours, to an atmosphere having a relative humidity of from 15% to 80% in order to improve polymorphic purity of the obtained masitinib mesylate crystal form M. Typically already the exposure to standard conditions will be sufficient.

Advantages

Crystalline form M of masitinib mesylate provides several benefits over the known crystalline form A. The present inventors have surprisingly found that crystal form M is less hygroscopic than form A.

As can be shown in Table 2 the water uptake between 15% RH and 80% RH is only from 0.5 w-% to 1.3 w-% for crystalline form M of masitinib mesylate, whereas crystalline form A of masitinib mesylate takes up from 4.0 w-% to 6.0 w-% water in the same range. In the range from 0% RH to 80% RH the water uptake for crystalline form M of masitinib mesylate was from 2.5 w-% to 3.3 w-%, in comparison to the 4.3 w-% described for DRX I.

Crystalline form M of masitinib mesylate also shows a relatively constant water content regardless the relative humidity of the surrounding atmosphere in the range of 15% RH and 80% RH. This also favors crystalline form M over crystalline form A as a form to be used for the preparation of a uniform drug product. For example crystalline form M of masitinib mesylate can be used at a range of relative humidity, which is typical of the regular working conditions encountered during finished dosage form preparation. Moreover, there is also no need for expensive packaging material, because the final drug product comprising crystalline form M is stable during storage in a relatively humid atmosphere of 80% relative humidity. In addition, crystalline form M of the present invention remains stable as crystalline form M for prolonged periods of time, such as for at least 8 weeks at 30° C. and 65% relative humidity or even for at least 8 weeks at 40° C. and 75% relative humidity.

Formulations

The present inventors have found that crystalline form M of the present invention demonstrates properties which render it surprisingly useful for the preparation of pharmaceutical compositions comprising crystalline form M. Crystalline form M of the invention may be formulated with one or more excipients or other active pharmaceutical ingredients to provide formulations suitable for the treatment of cancer, ALS or mast cell activation syndrome.

The present invention therefore also relates to pharmaceutical compositions comprising crystalline form M of the present invention. Such formulations may optionally include one or more other components selected, for example, from the group consisting of excipients, such as diluents, binders, disintegrants, lubricants, glidants, preservatives and coating materials, and other active pharmaceutical ingredients of different molecular structure. Preferably, the masitinib mesylate crystal form M of the present invention is kept at or below 40° C., such as below 30° C. or below 25° C. during preparation, formulation and storage.

Generally, there are no specific restrictions concerning the chemical nature of these excipients provided that the excipient or mixture of excipients comprised in the oral solid dosage form is/are pharmaceutically acceptable. A pharmaceutically acceptable excipient is an excipient which is relatively non-toxic and innocuous to a patient at concentrations consistent with effective activity of the masitinib mesylate crystal form M so that any side effects ascribable to the excipient do not vitiate the beneficial effects of the masitinib mesylate crystal form M. Therefore, according to the present invention, excipients are, for example, disintegrants, binders, lubricants, fillers, plasticizers, surfactants, glidants and wetting agents, film-forming agents and coating materials, sweeteners, flavoring agents, and coloring agents such as example pigments. Other excipients known in the field of pharmaceutical compositions may also be used. Excipients, which are compatible with dry formulation methods, i.e. formulation methods that avoid that a part of masitinib mesylate crystal form M gets dissolved during the formulation method, are preferred.

Disintegrants include, but are not limited to, carboxymethylcellulose calcium, carboxymethylcellulose sodium, croscarmellose (crosslinked carboxymethylcellulose) sodium, cross-linked polyvinylpyrrolidone, crospovidone (cross-linked povidone, a synthetic cross-linked homopolymer of N-vinyl-2-pyrrolidone), alginic acid, microcrystalline cellulose (such as refined wood pulp derived from alpha cellulose), hydroxypropyl cellulose, low substituted hydroxypropyl cellulose, polacrillin potassium, sodium alginate, sodium starch glycolate, partially hydrolysed starch, sodium carboxymethyl starch, and starch. Preferred disintegrants are croscarmellose (crosslinked carboxymethylcellulose) sodium, crospovidone (cross-linked povidone, a synthetic cross-linked homopolymer of N-vinyl-2-pyrrolidone), sodium starch glycolate, partially hydrolysed starch, sodium carboxymethyl starch, and starch, with crospovidone, sodium starch glycolate, and croscarmellose sodium being particularly preferred disintegrants.

Binders include, but are not limited to, hydroxypropyl cellulose, hypromellose (hydroxypropyl methylcellulose, HPMC), microcrystalline cellulose, acacia, alginic acid, carboxymethylcellulose, ethylcellulose, methylcellulose, hydroxyethylcellulose, ethylhydroxyethylcellulose, polyvinyl alcohol, polyacrylates, carboxymethylcellulose calcium, carboxymethylcellulose sodium, compressible sugar, ethylcellulose, methylcellulose, polyvinyl pyrrolidone and pregelatinized starch. Preferred binders are hydroxypropyl cellulose, hypromellose, microcrystalline cellulose, compressible sugar, pregelatinized starch, with microcrystalline cellulose and compressible sugar being particularly preferred.

Lubricants include, but are not limited to, calcium stearate, magnesium stearate, mineral oil, stearic acid, fumaric acid, sodium stearylfumarate, zinc stearate and polyethylene glycol. Preferred lubricants are magnesium stearate, stearic acid and sodium stearylfumarate, with magnesium stearate and sodium stearylfumarate being particularly preferred.

Fillers include, but are not limited to, dibasic calcium phosphate, kaolin, microcrystalline cellulose, silicated microcrystalline cellulose, dicalcium phosphate, tricalcium phosphate, magnesium trisilicate, lactose such as example the anhydrous form or the hydrate form such as the monohydrate form, sugars such as dextrose, maltose, saccharose, glucose, fructose or maltodextrine, sugar alcohols such as mannitol, maltitol, sorbitol, xylitol, powdered cellulose, precipitated calcium carbonate, sodium carbonate, sodium phosphate and starch. Preferred fillers are dibasic calcium phosphate, microcrystalline cellulose, lactose such as example the anhydrous form or the hydrate form such as the monohydrate form, sugars such as dextrose, maltose, saccharose, glucose, fructose or maltodextrine, sugar alcohols such as mannitol, maltitol, sorbitol, xylitol and powdered cellulose, with
microcrystalline cellulose, lactose such as for example the anhydrous form or the hydrate form such as the monohydrate form, sugars such as dextrose, maltose, saccharose, glucose, fructose or maltodextrine and sugar alcohols such as mannitol, maltitol, sorbitol, and xylitol, being particularly preferred. As a general guidance, fillers which are slightly hygroscopic or non-hygroscopic are preferred, with non-hygroscopic fillers being particularly preferred, in particular when the dosage form is to be used for tropical countries.

Surfactants and wetting agents may be included, in particular if disintegration of the tablet is to be improved. Examples are not limited to, heptadecaethylene oxycetanol, lecithins, sorbitol monooleate, polyoxyethylene sorbitol monooleate, polyoxyethylene stearate, polyoxyethylen sorbitan monolaurate, benzalkonium chloride, nonoxynol 10, oxtoxynol 9, polysorbates, for example polysorbate 20, polysorbate 40, polysorbate 60 or polysorbate 80, sorbitan monopalmitate, sodium salts of fatty alcoholsulfates such as sodium lauryl sulfate, sodium dodecylsulfate, sodium salts of sulfosuccinates such as sodium dioctylsulfosuccinate, partially esters of fatty acids with alcohols such as glycerine monostearate, partially esters of fatty acids with sorbitans such as sorbitan monolaurate, partially esters of fatty acids with polyhydroxyethylene sorbitans such as polyethyleneglycol sorbitan monolaurate, -monostearate or -monooleate, ethers of fatty alcohols with polyhydroxyethylene, esters of fatty acids with polyhydroxyethylene, copolymers of ethylenoxide and propylenoxide (Pluronic®) and ethoxylated triglycerides. In general, care should be taken to limit the use of liquid excipients as they might interfere with the dry granulation process.

Glidants include, but are not limited to, silica, colloidal silica, e.g. colloidal silica anhydrous, e.g. Aerosilâ 200, magnesium trisilicat, powdered cellulose, starch and talc. Colloidal silica anhydrous, talc or/and colloidal silicon dioxide are preferred glidants.

Plasticizers include, but are not limited to, polyethylene glycol, diethyl phthalate and glycerol. Preference is given to polyethylene glycol.

Tablet cores can be prepared from a mixture of masitinib mesylate and the above mentioned excipients, for example by direct compression. The present inventors have, however, found out that a dry granulate of masitinib mesylate crystal form M shows improved processing properties compared with the masitinib mesylate crystal form M per se, in particular improved flowability. Thus, the present invention also relates to a dry granulate comprising masitinib mesylate crystal form M, and in particular further comprising an excipient, such as preferably a binder. A preferred dry granulate comprising masitinib mesylate crystal form M and a binder is a dry granulate wherein the binder is selected from a cellulose, a cellulose derivative and a compressible sugar, such as from microcrystalline cellulose and a compressible sugar, for example lactose. The dry granulate is the mixed with further excipients and tablet cores can be prepared from the resulting mixture. Tablet cores can be filmed, preferably after having bee further coated by a filler, for example by microcrystalline cellulose, or tablet cores may be used directly without film coating. Film-forming agents and coating materials include, but are not limited to, liquid glucose, hydroxyethyl cellulose, hydroxypropyl cellulose, hydroxypropyl methylcellulose (hypromellose, HPMC), methylcellulose, ethylcellulose, cellulose acetate phthalate, shellac, polyvinylpyrrolidone, copolymers of vinylpyrrolidone and vinylacetate such as Kollidon® VA64 BASF, copolymers of acrylic and/or methacrylic acid esters with trimethylammoniummethylacrylate, copolymers of dimethylaminomethacrylic acid and neutral methacrylic acid esters, polymers of methacrylic acid or methacrylic acid esters, copolymers of acrylic acid ethylester and methacrylic acid methyl ester, and copolymers of acrylic acid and acrylic acid methylester.

Preferred film-forming agents and coating materials are hydroxypropyl cellulose, hydroxypropyl methylcellulose (hypromellose, HPMC), and partically hydrolyzed polyvinyl alcohol, but also commercially available ready to use mixtures, such as Opadry II, can be used.

Coloring agents invention include, but are not limited to, pigments, inorganic pigments, FD&C Red No. 3, FD&C Red No. 20, FD&C Yellow No. 6, FD&C Blue No. 2, D&C Green No. 5, D&C Orange No. 5, D&C Red No. 8, caramel, ferric oxide red, ferric oxide yellow and titanium dioxide.

Further commonly used excipients which may be used include, but are not limited to, acidifying agents such as acetic acid, citric acid; alkalizing agents such as ammonia solution, ammonium carbonate, diethanolamine, monoethanolamine, potassium hydroxide, sodium borate, sodium carbonate, sodium hydroxide, triethanolamine and trolamine; adsorbents such as powdered cellulose and activated charcoal; stabilizers and antioxidants such as ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate and sodium metabisulfite; binding materials such as block polymers, natural and synthetic rubber, polyacrylates, polyurethanes, silicones, polysiloxanes and styrene-butadiene copolymers; buffering agents such as potassium metaphosphate, dipotassium phosphate, sodium acetate, sodium citrate anhydrous and sodium citrate hydrates; encapsulating agents such as gelatin, starch and cellulose derivates; flavorants, masking agents and odors such as anise oil, cinnamon oil, cocoa, menthol, orange oil, peppermint oil and vanillin; humectants such as glycerol, propylene glycol and sorbitol; sweeteners such as aspartame, dextrose, glycerol, mannitol, propylene glycol, saccharin sodium, sorbitol and sucrose; anti-adherents such as magnesium stearate and talc; direct compression excipients such as dibasic calcium phosphate, lactose and microcrystalline cellulose; tablet polishing agents such as carnauba wax and white wax.

The skilled person will appreciate that depending upon formulation context and concentration a particular excipient can fulfill various and sometimes even different functions. For example, microcrystalline cellulose is a particular hydrolyzed cellulose, which can be used as a filler, binder and/or disintegrating material in tablet production, dependent on formulation context and concentration. Reference is made to the literature on pharmaceutical excipients and pharmaceutical formulation, such as Fiedler Encyclopedia of Excipients for Pharmaceuticals, Cosmetics and Related Areas. Wissenschaftliche Verlagsgesellschaft Stuttgart, 2013, Bauer, Frömming and Führer, "Lehrbuch der Pharmazeutischen Technologie" Wissenschaftliche Verlagsgesellschaft Stuttgart, 9. Auflage (2012) or—with a particular focus on tablet production-Augsburger and Stephen, Pharmaceutical Dosage Forms: Tablets, Third Edition, Volume 2, Informa Healthcare (2008). The skilled person will therefore appreciate that terms like "disintegrant", "binder", "lubricant", "filler", "plasticizer", "surfactant", "wetting agent", "film-forming agent", "coating material", "sweetener", "flavoring agent" and "coloring agent" are primarily functional definitions and that the structural characterization provided above are given so as to more easily allow identification of suitable excipients.

Preferred pharmaceutical compositions are solid oral dosage forms, such as capsules or tablets, with tablets being particularly preferred.

The present inventors have noticed that even though the crystal form M of the present invention itself is storage stable even at stress conditions of 40° C./75% relative humidity, care should be taken during the formulation process so as to enable the preparation of storage stable pharmaceutical compositions comprising crystal form M of the present invention. Tablets prepared by wet granulation were found to demonstrate a time dependent appearance of form I upon storage. This (partial) polymorphic conversion of crystal form M of the present invention to crystal form I could be prevented when a dry formulation method, i.e. a formulation method that avoid that a part of masitinib mesylate crystal form M got dissolved during the formulation method, was used. Tablets prepared by direct compression or by dry granulation methods did not show even partial conversion of crystal form M, which remained polymorphically stable in formulations prepared by dry methods even upon prolonged storage.

In a preferred embodiment the present invention therefore relates to an oral solid dosage form comprising masitinib mesylate crystal form M, wherein the oral solid dosage form was not prepared by a method comprising a wet granulation step. Preferably the oral solid dosage form, such as a tablet, was prepared by dry granulation or direct compression.

The present invention also relates to a process for the preparation of a pharmaceutical composition comprising masitinib mesylate crystal form M wherein the formulation process does not comprise wet granulation. In particular, the formulation process is a direct compression process or comprises a dry granulation step.

The bulk density of masitinib mesylate crystal form M is relatively low (0.14 g/mL). Thus, while direct compression is possible, the present inventors found that dry compaction of the masitinib mesylate form M prior to or in a first step of the formulation process improved handling and processing significantly. Thus, a process for the preparation of a pharmaceutical composition comprising masitinib mesylate crystal form M wherein the formulation process comprises a dry granulation process, such as roller compaction, is particularly preferred.

A formulation example for film coated tablets: tablet cores can be prepared from 100 mg masitinib mesylate crystal form M, 211.5 mg microcrystalline cellulose (e.g. Avicel® PH102), 4.4 g Aerosil® 200, 3.2 mg sodium stearylfumarate, 2.9 mg sodium starch glycolate. Tablet cores are then film coated (e.g. by using an Opadry II coating mixture (30 mg)).

A formulation example for film coated tablets: tablet cores can be prepared from 100 mg masitinib mesylate crystal form M, 203.2 mg lactose monohydrate (e.g. Tablettose® 70), 3.4 mg magnesium stearate, 7.7 mg crosslinked povidone and 7.7 mg Povidone K30. Tablet cores are then film coated (e.g. by using an Opadry II coating mixture (30 mg)).

It was surprising to find that crystal form M of the present invention is useful for the preparation of tablets which can be stored for longer periods of time without the detection of polymorphic conversion of crystal form M. The present inventors have discovered that storage of form M at or below 40° C. and at a relative humidity of from 15% RH to 75% RH does not result in polymorphic conversion. Thus, the present invention also relates to the use of masitinib mesylate crystal form M for the preparation of an oral solid dosage form, e.g. a tablet, wherein the masitinib mesylate crystal form M does not transform to any other solid form of masitinib mesylate when the tablets are stored at 25° C. at a relative humidity of 60% for a period of at least 30 days. The present invention also relates to the use of masitinib mesylate crystal form M for the preparation of an oral solid dosage form, e.g. a tablet, wherein the masitinib mesylate crystal form M does not transform to any other solid form of masitinib mesylate when the tablets are stored at 30° C. at a relative humidity of 65% for a period of at least 30 days. The present invention also relates to the use of masitinib mesylate crystal form M for the preparation of an oral solid dosage form, e.g. a tablet, wherein the masitinib mesylate crystal form M does not transform to any other solid form of masitinib mesylate when the tablets are stored at 40° C. at a relative humidity of 75% for a period of at least 30 days.

The present invention also relates to tablets, wherein the tablets have been prepared at least 30 days ago and comprising masitinib mesylate crystal form M in substantially pure form as the only solid form of masitinib mesylate. Preferably, crystal form M includes less than 5 w-%, more preferably less than 3 w-%, even more preferably less than 2 w-%, most preferably less than 1% by weight of crystal form I.

Accordingly, the present invention also provides the following aspects, subject-matters and preferred embodiments which, respectively taken alone or in combination, contribute to providing improved technical effects and to solving the afore-mentioned object of the invention:

1. A crystalline form of masitinib mesylate characterized by an x-ray powder diffraction pattern comprising reflections at 2-Theta angles of 8.6±0.2°, 9.4±0.2°, 9.7±0.2°, 12.3±0.2° and 17.2±0.2°, when measured at room temperature using Cu—K$\alpha_{1,2}$ radiation having a wavelength of 0.15419 nm.

2. A crystalline form of masitinib mesylate characterized by an x-ray powder diffraction pattern comprising reflections at 2-Theta angles of 8.6±0.1°, 9.4±0.1°, 9.7±0.1°, 12.3±0.1° and 17.2±0.1°, when measured at room temperature using Cu—K$\alpha_{1,2}$ radiation having a wavelength of 0.15419 nm.

3. The crystalline form according to item 1 further characterized by at least one additional reflection at a 2-Theta angle selected from 12.0±0.2°, 16.1±0.2°, 16.5±0.2°, 17.5±0.2°, 17.8±0.2°, 18.4±0.2° and/or 20.7±0.2°, when measured at room temperature with Cu—K$\alpha_{1,2}$ radiation having a wavelength of 0.15419 nm.

4. The crystalline form according to item 2 further characterized by at least one additional reflection at a 2-Theta angle selected from 12.0±0.1°, 16.1±0.1°, 16.5±0.1°, 17.5±0.1°, 17.8±0.1°, 18.4±0.1° and/or 20.7±0.1°, when measured at room temperature with Cu—K$\alpha_{1,2}$ radiation having a wavelength of 0.15419 nm.

5. A crystalline form of masitinib mesylate characterized by having a XRPD pattern comprising five or more reflections, such as 6 reflections, 7 reflections, 8 reflections or 10 reflections, at 2-Theta angles selected from 8.6±0.2°, 9.4±0.2°, 9.7±0.2°, 12.0±0.2°, 12.3±0.2°, 16.1±0.2°, 16.5±0.2°, 17.2±0.2°, 17.5±0.2°, 17.8±0.2°, 18.4±0.2° and 20.7±0.2°, when measured at room temperature with Cu—K$\alpha_{1,2}$ radiation having a wavelength of 0.15419 nm.

6. A crystalline form of masitinib mesylate characterized by having a XRPD pattern comprising five or more reflections such as 6 reflections, 7 reflections, 8 reflections or 10 reflections, at 2-Theta angles selected from 8.6±0.1°, 9.4±0.1°, 9.7±0.1°, 12.0±0.1°, 12.3±0.1°, 16.1±0.1°, 16.5±0.1°, 17.2±0.1°, 17.5±0.1°, 17.8±0.1°, 18.4±0.1° and 20.7±0.1°, when measured at room temperature with Cu—K$\alpha_{1,2}$ radiation having a wavelength of 0.15419 nm.

7. The crystalline form according to any one of items 1 to 6 wherein the water content is from 0.1 w-% to 2.5 w-%.

8. The crystalline form according to any one of items 1 to 7 in substantially pure form.

9. The crystalline form according to any one of items 1 to 8 further characterized by comprising no significant reflection at a 2-Theta angle of 11.04°.

10. The crystalline form according to any one of items 1 to 8 comprising less than 10 w-%, preferably less than 5 w-%, more preferably less than 3 w-%, most preferably less than 1 w-% of masitinib mesylate crystal form I, wherein form I is characterized by a x-ray powder diffraction pattern comprising peaks at 2-Theta values of 11.04, 14.48, 16.72, 18.22 and 19.25.

11. The crystalline form according to any one of items 1 to 10 further characterized by comprising no significant reflection at a 2-Theta angle of 21.1°±0.2°.

12. The crystalline form according to any one of items 1 to 10 comprising less than 10 w-%, preferably less than 5 w-%, more preferably less than 3 w-%, most preferably less than 1 w-% of masitinib mesylate crystal form A, wherein form A is characterized by a x-ray powder diffraction pattern comprising peaks at 2-Theta values of 20.7°, 18.2° and 21.1°.

13. The crystalline form according to any one of items 1 to 12 or the pharmaceutical composition according to any one of items 20 to 26 for use in the treatment of cancer, inflammatory diseases, mast cell activation syndrome and CNS disorders in human subjects, and in the treatment of mastocytosis in dogs.

14. A process for the preparation of the crystalline form of items 1-12 comprising the steps of
i) providing masitinib free base
ii) (a) dissolving or suspending the material provided in (i) in methanol comprising water and (b) adding methane sulfonic acid,
iii) optionally seeding the mixture with the crystalline form of masitinib mesylate and
iv) subjecting the mixture provided in (iii) to crystallization conditions leading to the formation of a crystalline form of masitinib mesylate
v) isolating the crystalline form of masitinib mesylate,
vi) drying the crystalline form of masitinib mesylate, and
vii) optionally equilibrating the crystalline form of masitinib mesylate with an atmosphere having a relative humidity of from 15% to 80% at a temperature of from 0° C. to 25° C.

15. A process for the preparation of the crystalline form of items 1-12 comprising the steps of
i') providing amorphous masitinib mesylate
ii') dissolving or suspending the material provided in (i') in methanol comprising water
iii') optionally seeding the mixture with the crystalline form of masitinib mesylate and
iv') subjecting the mixture provided in (iii') to crystallization conditions leading to the formation of a crystalline form of masitinib mesylate
v') isolating the crystalline form of masitinib mesylate,
vi') drying the crystalline form of masitinib mesylate, and
vii') optionally equilibrating the crystalline form of masitinib mesylate with an atmosphere having a relative humidity of from 15% to 80% at a temperature of from 0° C. to 25° C.

16. The process of items 14 or 15, wherein the crystallization of masitinib mesylate is in the presence of a methanol/water mixture.

17. The process of any one of items 14 to 16, wherein drying is at a temperature of at most 25° C. and at reduced pressure of at most 50 mbar, such as at most 30 mbar.

18. The process of any one of items 14 to 17, wherein step vii) or vii') is with an atmosphere having a relative humidity of 40% and at a temperature of 20° C.

19. Crystalline masitinib mesylate obtainable by the process of any one of items 14 to 18.

20. A pharmaceutical composition comprising the crystalline masitinib mesylate form M according to any one of items 1 to 12 and a pharmaceutically acceptable carrier or diluent.

21. The pharmaceutical composition of item 20 which is a solid oral dosage forms, such as a capsule or tablet, preferably a tablet.

22. The pharmaceutical composition of item 21, which is not a wet-granulation tablet.

23. The pharmaceutical composition of item 21, which is a dry granulation tablet or a direct compression tablet.

24. The pharmaceutical composition of any one of items 20 to 23, wherein the masitinib mesylate crystal form M does not transform to any other solid form of masitinib mesylate when the pharmaceutical composition is stored at 25° C. at a relative humidity of 60% for a period of at least 30 days.

25. The pharmaceutical composition of any one of items 20 to 24, wherein the masitinib mesylate crystal form M does not transform to any other solid form of masitinib mesylate when the pharmaceutical composition, for example a tablet, is stored at 30° C. at a relative humidity of 65% for a period of at least 30 days.

26. The pharmaceutical composition of any one of items 20 to 25, wherein the masitinib mesylate crystal form M does not transform to any other solid form of masitinib mesylate when the pharmaceutical composition, for example a tablet, is stored at 40° C. at a relative humidity of 75% for a period of at least 30 days.

27. A process for the preparation of a pharmaceutical composition according to any one of items 20 to 26, wherein crystalline masitinib mesylate is mixed with at least one excipient and further processed to a pharmaceutical composition, the process not comprising a wet granulation step.

28. The process of item 27, wherein the process comprises a dry granulation step, such as roller compaction.

29. Use of masitinib mesylate crystal form M for the preparation of an oral solid dosage form, e.g. a tablet, wherein the masitinib mesylate crystal form M does not transform to any other solid form of masitinib mesylate when the tablets are stored at 25° C. at a relative humidity of 60% for a period of at least 30 days.

30. Use of masitinib mesylate crystal form M for the preparation of an oral solid dosage form, e.g. a tablet, wherein the masitinib mesylate crystal form M does not transform to any other solid form of masitinib mesylate when the tablets are stored at 30° C. at a relative humidity of 65% for a period of at least 30 days.

31. Use of masitinib mesylate crystal form M for the preparation of an oral solid dosage form, e.g. a tablet, wherein the masitinib mesylate crystal form M does not transform to any other solid form of masitinib mesylate when the tablets are stored at 40° C. at a relative humidity of 75% for a period of at least 30 days.

32. The crystalline form according to any one of items 1 to 12 comprising at most 0.20 w-% methanol.

33. The crystalline form according to any one of items 1 to 12 comprising at most 0.15 w-% methanol.

X-Ray Powder Diffraction (XRPD)

X-Ray powder diffraction (XRPD) was performed with a PANalytical X'Pert PRO diffractometer equipped with a theta/theta coupled goniometer in transmission geometry, Cu—K$\alpha$1,2 radiation (wavelength 0.15419 nm) with a focusing mirror and a solid state PIXcel detector. Diffractograms were recorded at a tube voltage of 45 kV and a tube current of 40 mA, applying a stepsize of 0.013° 2-Theta with 40 s per step (255 channels) in the angular range of 2° to 40° 2-Theta at ambient conditions.

Gravimetric Moisture Sorption/Desorption

Gravimetric moisture sorption/desorption (GMSD) isotherms were recorded with an SPSx-1μ moisture sorption analyzer (ProUmid, Ulm). The measurement cycle was started at ambient relative humidity (RH) of 25%. Relative humidity was then decreased to 5% RH in 5% steps, followed by a further decrease to 3% RH and to 0% RH. Afterwards RH was increased from 0% to 80% RH in a sorption cycle in 5% steps.

The time per step was set to a minimum of 2 hours and a maximum of 6 hours. If an equilibrium condition with a constant mass of ±0.01% within 1 hour was reached before the maximum time for all examined samples the sequential humidity step was applied before the maximum time of 6 hours. If no equilibrium was achieved the consecutive humidity step was applied after the maximum time of 6 hours. The temperature was 25±0.1° C.

While the present invention has been described with respect to some preferred embodiments, this is in no way to limit the scope of the invention. The person skilled in the art is clearly aware of further embodiments and variations to the above-described embodiments which are still within the scope of the present invention.

The following non-limiting examples are illustrative of the disclosure, but are not to be used to be in any way limiting to the scope of the present invention.

EXAMPLES

Example 1: Preparation of the Crystalline Form M from Masitinib Free Base

Example 1-1

100 mg Masitinib were dissolved in 0.6 mL non-anhydrous methanol at room temperature, followed by addition of 14.3 μL methanesulfonic acid. The solution was stirred at room temperature for 18 h, leading to the formation of a slurry. Afterwards, the solid material was collected by filtration and dried at room temperature under vacuum (about 30 mbar) to yield crystalline form M of masitinib mesylate. Characteristic PXRD pattern of the obtained crystalline form is shown in FIG. 1.

Example 1-2

100 mg Masitinib were dissolved in 0.6 mL non-anhydrous methanol at room temperature. The solution was cooled to a temperature of from 0 to 5° C., followed by addition of 14.3 μL methanesulfonic acid. The solution was stirred at a temperature of from 0 to 5° C. for 18 h, leading to the formation of a slurry. Afterwards, the solid material was collected by filtration and dried at room temperature under vacuum (about 30 mbar) to yield crystalline form M of masitinib mesylate.

Example 1-3

100 mg Masitinib were dissolved in 0.6 mL non-anhydrous methanol at room temperature. The solution was cooled to a temperature of from 0 to 5° C., followed by addition of 14.3 μL methanesulfonic acid. 2.6 mg of seed crystals of crystalline form M of masitinib mesylate, prepared according to Example 1.1, were added under stirring, leading to the direct formation of a slurry. The mixture was further stirred at a temperature of from 0 to 5° C. for 18 h. Afterwards, the solid material was collected by filtration and dried at room temperature under vacuum (about 30 mbar) to yield crystalline form M of masitinib mesylate.

Example 1-4

8.6 g Masitinib were dissolved in 48 mL non-anhydrous methanol at room temperature under stirring, followed by addition of 1.1 mL methanesulfonic acid. The solution was stirred at 25° C. for 13 hours, leading to the formation of a slurry. The slurry was cooled to 4° C. over 4 hours under stirring conditions and further stirred at 4° C. for 1 hour. Afterwards, the solid material was collected by filtration and dried at room temperature under vacuum (about 30 mbar) to yield plate to prism-shaped crystalline form M of masitinib mesylate (8.5 g) as a white powder.

Example 2: Preparation of Crystalline Form M from Amorphous Masitinib Mesylate

Example 2-1

100 mg amorphous masitinib mesylate were dissolved in 0.6 mL non-anhydrous methanol at room temperature under stirring conditions. After a few seconds, precipitation took place leading to the formation of a white slurry. The mixture was further stirred at room temperature for 18 h. Afterwards, the solid material was collected by filtration and dried at room temperature under vacuum (about 30 mbar) to yield crystalline form M of masitinib mesylate.

Example 2-2

50 mg amorphous masitinib mesylate were dissolved in 0.6 mL non-anhydrous methanol at room temperature under stirring conditions. After a few seconds, precipitation took place leading to the formation of a white slurry. The mixture was further stirred at room temperature for 18 h. Afterwards, the solid material was collected by filtration and dried at room temperature under vacuum (about 30 mbar) to yield crystalline form M of masitinib mesylate.

Example 2-3

To 2.19 g amorphous masitinib mesylate were added 13 mL non-anhydrous methanol at room temperature. The mixture was stirring at 25° C. allowing a fast sample dissolution/crystallization process. The slurry was stirred at 25° C. for 14 hours and cooled to 5° C. over 4 hours under stirring conditions. Afterwards, the solid material was collected by filtration, washed with cold methanol and dried at room temperature under vacuum (about 30 mbar) to yield crystalline form M of masitinib mesylate (1.82 g) as a white powder.

Preparatory Example: Preparation of Amorphous Masitinib Mesylate 2.0 g Masitinib mesylate (for example prepared according to the procedure disclosed in WO 2008/098949 A2) were dissolved in 35 mL acetonitrile/water (volume ratio 1:1) and 10 mL water, followed by filtration with the aid of a syringe filter (pore size 0.45 microns). The homogeneous solution was frozen in a bath of liquid nitrogen and lyophilized at room temperature and a pressure of from 0 to 2 mbar, yielding amorphous masitinib mesylate as a white solid.

Example 3

Preparation of Tablets by Wet Granulation.

Preparation of granulation agent: 0.9 g of polyvinylpyrrolidone were dissolved in 8.25 g ethanol 96% until a clear solution was obtained. 5.0 g Masitinib mesylate form M and 9.0 g microcrystalline cellulose (e.g. Avicel® PH102) were mixed by using a mortar and pistil for 5 min. The granulation agent was applied dropwise to the dry mixture of masitinib mesylate and microcrystalline cellulose. The wet granules were dried for 30 min at 30° C. (tray drying). The dry granules were then sieved (0.8 mm sieve).

To the obtained granulate (14.9 g) 1.1 g Kollidon CL® and 0.2 g Mg-stearate were added. The blend was mixed for 5 min by using a Turbula mixer.

Figure 3:
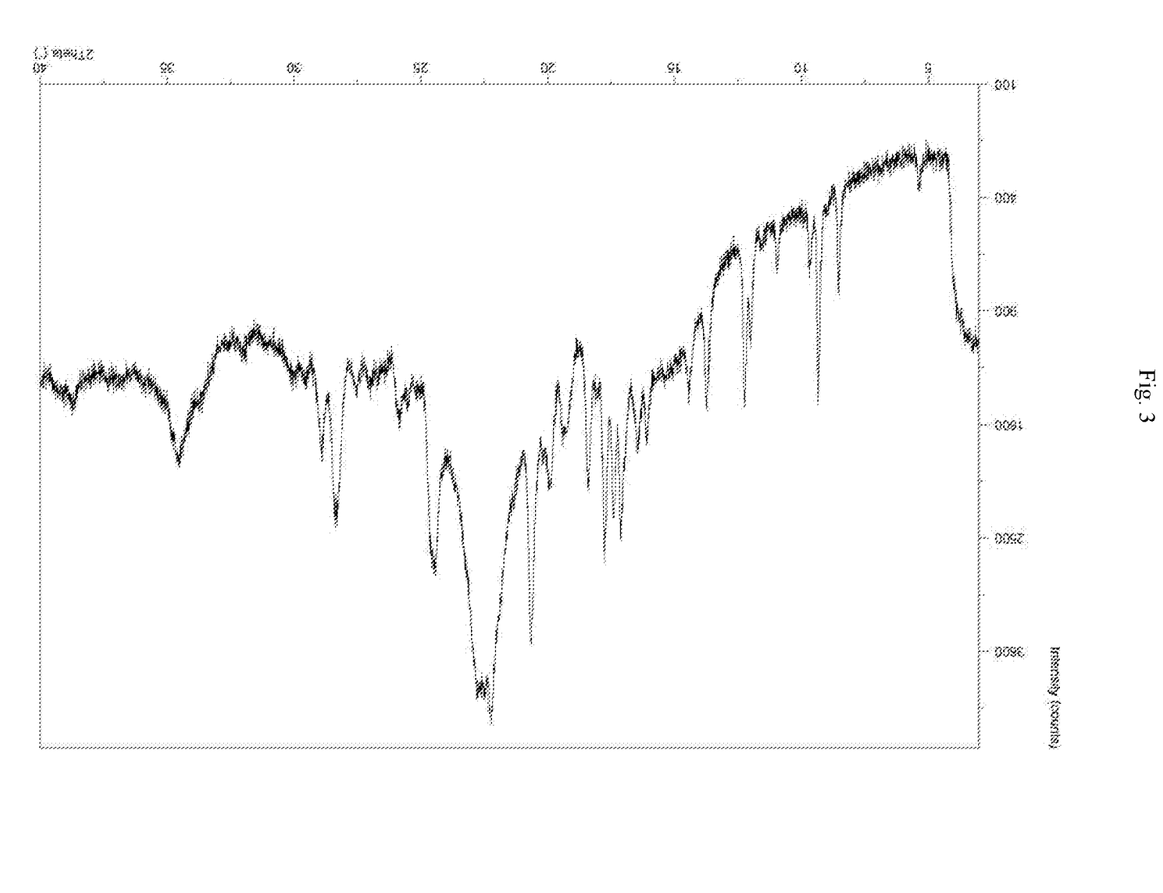
FIG. 3 illustrates the x-ray powder diffraction pattern of tablets of example 3 comprising crystalline form M of masitinib mesylate and prepared by wet granulation

Tablets were compressed by using a Korsch XP1 tablet press and analyzed by XRPD. Part of crystalline form M had converted to crystal form I as evident from the appearance of a peak at 11.2° 2-Theta as shown in FIG. 3.

Example 4

Preparation of Tablets by Direct Compression.

5.0 g Masitinib mesylate from M and 11.2 g PROSOLV® EASYtab SP Ready to use tableting mixture (a ready-to-use excipient composite of microcrystalline cellulose, colloidal silicon dioxide, sodium starch glycolate and sodium stearyl fumarate having a bulk density of 0.30-0.42 g/ml obtainable from JRS Pharma, Rosenberg (Germany)), were sieved (0.8 mm sieve) and mixed for 5 min by using a Turbula mixer.

Figure 4:
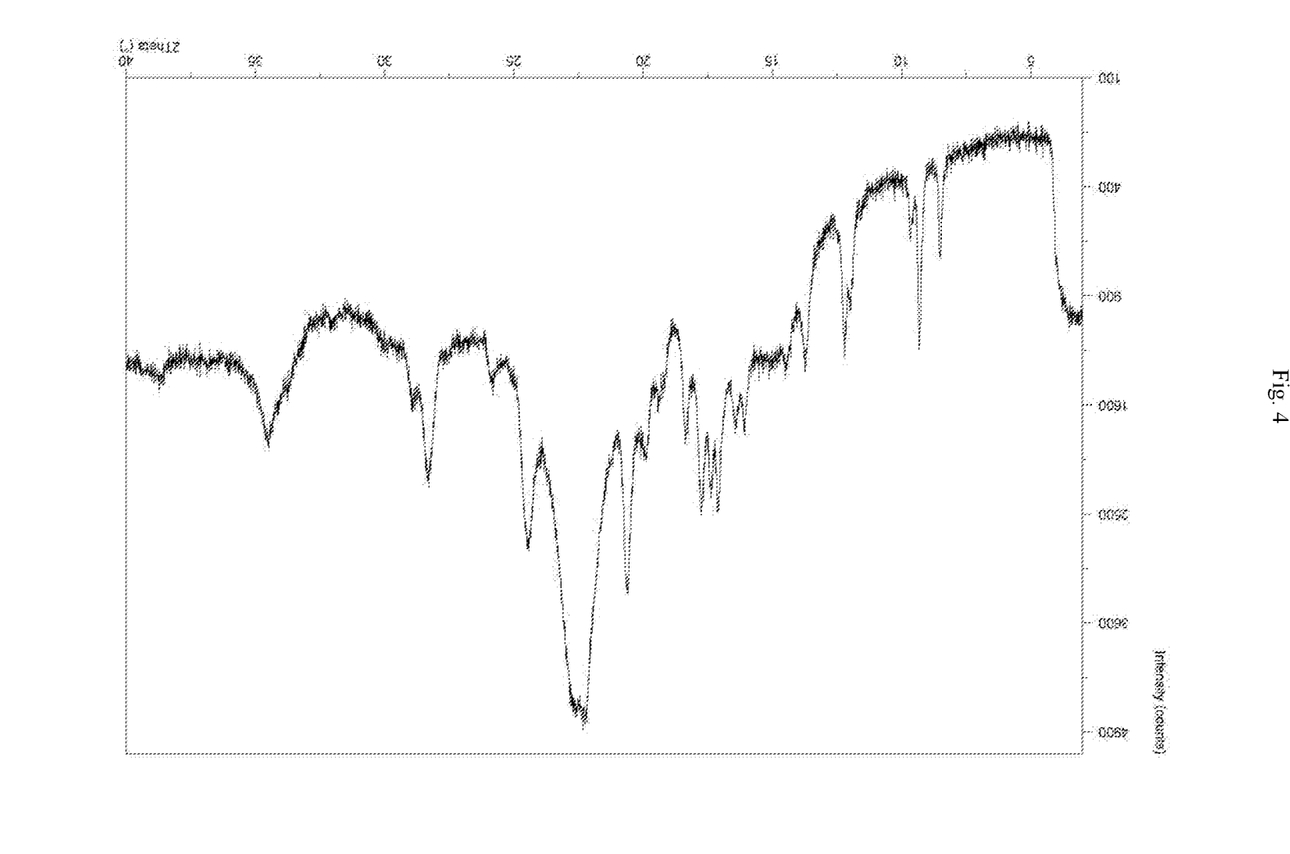
FIG. 4 illustrates the x-ray powder diffraction pattern of tablets of example 4 comprising crystalline form M of masitinib mesylate and prepared by direct compression

Tablets were compressed by using a Korsch XP1 tablet press and analyzed by XRPD. No conversion to crystal form I was detectable as evident from the lack of a peak at 11.2° 2-Theta as shown in FIG. 4.

Example 5

Preparation of Tablets by Direct Compression.

5.0 g Masitinib mesylate form M, 10.0 g Ludipress® ready to use tableting mixture (a low hygroscopicity/high flowability mixture of lactose monohydrate, povidine [Kollidon 30®] and crospovidone [Kollidon CL®] obtainable from BASF) and 0.2 g magnesiumstearate were sieved (0.8 mm sieve) and mixed for 5 min by using a Turbula mixer.

Tablets were compressed by using a Korsch XP1 tablet press and analyzed by XRPD. No conversion to crystal form I was detectable as evident from the lack of a peak at 11.2° 2-Theta.

Example 6

Preparation of Tablets by Roller Compaction and Compression

Masitinib mesylate form M (16.8 g) and microcrystalline cellulose (e.g. Avicel® PH102) (27.1 g) were sieved (0.8 mm) and mixed by using a Turbula mixer. The mixture was compacted on a Vector and Freund TFC Lab Micro roller compactor.

The parameters for the compaction were set as follows:
Roller speed: 2 rpm
Roller pressure: 7 MPa
Screens: 1.0 mm The resulting dry granulate showed improved flowability compared to masitinib mesylate crystal form M per se.

The resulting dry granulate constituted the intragranular phase in subsequent tableting.

41 g granulate were mixed with 7.8 g microcrystalline cellulose (e.g. Avicel®), 0.7 g Silicon dioxide (e.g. Aerosil®) and 0.5 g sodium starch glycolate for 7 min by using a Turbula mixer. 0.5 g Sodium stearyl fumarate was added to the mixture and mixed for additional 3 min by using a Turbula mixer. Tablets were compressed by using a Korsch XP1 tablet press and analyzed by XRPD. No conversion to crystal form I was detectable as evident from the lack of a peak at 11.2° 2 Theta.

Example 7

Preparation of Tablets by Roller Compaction and Compression

Masitinib mesylate form M (15.1 g) and 23.2 g lactose monohydrate (e.g. Tablettose 70) were sieved (1.0 mm) and mixed by using a Turbula mixer. The mixture was compacted on a Vector and Freund TFC Lab Micro roller compactor.

The parameters for the compaction were set as follows:
Roller speed: 2 rpm
Roller pressure: 7 MPa
Screens: 1.0 mm The resulting dry granulate showed improved flowability compared to masitinib mesylate crystal form M per se.

The resulting granulate constituted the intragranular phase in subsequent tableting.

Figure 5:
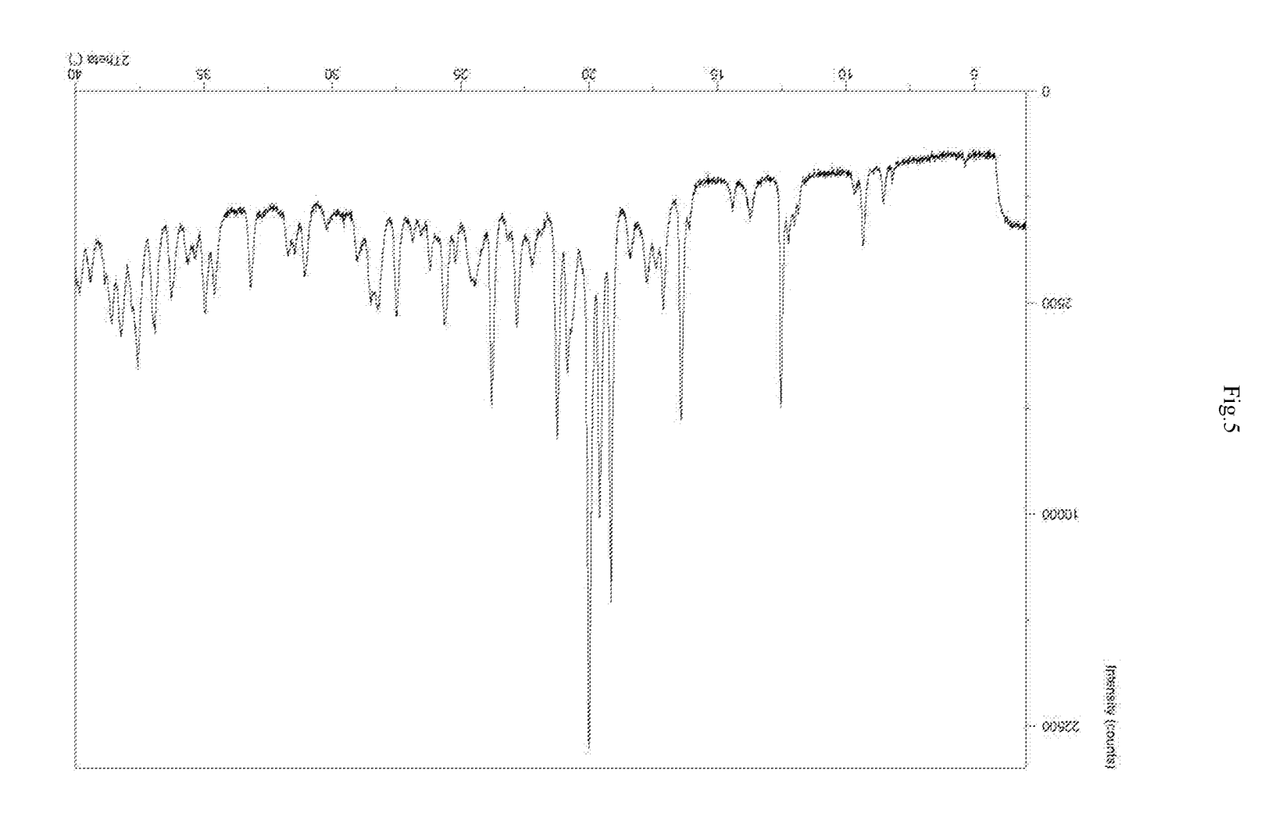
FIG. 5 illustrates the x-ray powder diffraction pattern of tablets of example 7 comprising crystalline form M of masitinib mesylate and prepared by roller compaction and compression

36.5 g granulate were mixed with 7.2 g lactose monohydrate (e.g. Tablettose 70), 1.1 g Povidone 30 and 1.1 g crosslinked Povidone for 7 min by using a Turbula mixer. 0.5 g magnesiumstearate was added to the mixture and mixed for additional 3 min by using a Turbula mixer. Tablets were compressed by using a Korsch XP1 tablet press and analyzed by XRPD. No conversion to crystal form I was detectable as evident from the lack of a peak at 11.2° 2 Theta as shown in FIG. 5. The tablets of example 7 showed faster dissolution than the tablets of example 6.

What is claimed is:

1. A crystalline form of masitinib mesylate characterized by an x-ray powder diffraction pattern comprising reflections at 2-Theta angles of 8.6±0.1°, 9.4±0.1°, 9.7±0.1°, 12.3±0.1° and 17.2±0.1°, when measured at room temperature using Cu-K$\alpha_{1,2}$ radiation having a wavelength of 0.15419 nm.

2. The crystalline form according to claim 1 wherein the water content is from 0.1 w-% to 2.5 w-%.

3. The crystalline form according to claim 1 wherein the methanol content is at most 0.20 w-%.

4. The crystalline form according to claim 1 further characterized by comprising no significant reflection at a 2-Theta angle of 11.04°±0.03°.

5. A process for the preparation of the crystalline form according to claim 1 comprising the steps of
   i) providing masitinib free base
   ii) (a) dissolving or suspending the material provided in (i) in methanol comprising water and (b) adding methane sulfonic acid,
   iii) optionally seeding the mixture with the crystalline form of masitinib mesylate according to claim 1 and
   iv) subjecting the mixture provided in (iii) to crystallization conditions leading to the formation of a crystalline form of masitinib mesylate
   v) isolating the crystalline form of masitinib mesylate,
   vi) drying the crystalline form of masitinib mesylate, and
   vii) optionally equilibrating the crystalline form of masitinib mesylate with an atmosphere having a relative humidity of from 15% to 80% at a temperature of from 0° C. to 25° C.

6. A process for the preparation of the crystalline form according to claim 1 comprising the steps of
   i') providing amorphous masitinib mesylate
   ii') dissolving or suspending the material provided in (i') in methanol comprising water
   iii') optionally seeding the mixture with the crystalline form of masitinib mesylate according to claim 1 and
   iv') subjecting the mixture provided in (iii') to crystallization conditions leading to the formation of a crystalline form of masitinib mesylate
   v') isolating the crystalline form of masitinib mesylate,
   vi') drying the crystalline form of masitinib mesylate, and
   vii') optionally equilibrating the crystalline form of masitinib mesylate with an atmosphere having a relative humidity of from 15% to 80% at a temperature of from 0° C. to 25° C.

7. The process of claim 5, wherein drying is at a temperature of at most 25° C. and at a reduced pressure of at most 50 mbar.

8. The process of claim 5, wherein step vii) or vii') is equilibrating with an atmosphere having a relative humidity of 40% and at a temperature of 20° C.

9. A pharmaceutical composition comprising the crystalline masitinib mesylate form M according to claim 1 and a pharmaceutically acceptable carrier or diluent.

10. The pharmaceutical composition of claim 9 which is a solid oral dosage forms.

11. The pharmaceutical composition of claim 10, which is not a wet-granulation tablet.

12. The pharmaceutical composition of claim 9, wherein the masitinib mesylate crystal form M does not transform to any other solid form of masitinib mesylate when the pharmaceutical composition is stored at 30° C. at a relative humidity of 65% for a period of at least 30 days.

13. A process for the preparation of a pharmaceutical composition according to claim 9, wherein crystalline masitinib mesylate is mixed with at least one excipient and further processed to a pharmaceutical composition, the process not comprising a wet granulation step.

14. The process of claim 13, wherein the process comprises a dry granulation step.

* * * * *